US010300469B1

(12) United States Patent
Huang et al.

(10) Patent No.: US 10,300,469 B1
(45) Date of Patent: May 28, 2019

(54) METAL-LIGAND COOPERATIVE CATALYSIS THROUGH N-H ARM DEPROTONATION/PYRIDINE DEAROMATIZTION FOR EFFICIENT HYDROGEN GENERATION FROM FORMIC ACID

(71) Applicant: KING ABDULLAH UNIVERSITY OF SCIENCE AND TECHNOLOGY, Thuwal (SA)

(72) Inventors: Kuo-Wei Huang, Thuwal (SA); Chengling Pan, Thuwal (SA); Yupeng Pan, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 38 days.

(21) Appl. No.: 15/101,342

(22) PCT Filed: Nov. 26, 2014

(86) PCT No.: PCT/IB2014/003120
§ 371 (c)(1),
(2) Date: Jun. 2, 2016

(87) PCT Pub. No.: WO2015/083007
PCT Pub. Date: Jun. 11, 2015

Related U.S. Application Data

(60) Provisional application No. 61/910,530, filed on Dec. 2, 2013.

(51) Int. Cl.
*B01J 31/18* (2006.01)
*C01B 3/22* (2006.01)
*C07F 15/00* (2006.01)

(52) U.S. Cl.
CPC ............ *B01J 31/189* (2013.01); *C01B 3/22* (2013.01); *C07F 15/0046* (2013.01); *B01J 2231/005* (2013.01); *B01J 2531/821* (2013.01); *C01B 2203/0277* (2013.01); *C01B 2203/1064* (2013.01); *C01B 2203/1211* (2013.01)

(58) Field of Classification Search
CPC .................................. B01J 31/189; C01B 3/22
See application file for complete search history.

(56) References Cited

U.S. PATENT DOCUMENTS

2012/0323007 A1    12/2012    Huang et al.

FOREIGN PATENT DOCUMENTS

EP    2644611 A1    10/2013
EP    2810711 A1    12/2014
WO    2013/111860 A1    8/2013

OTHER PUBLICATIONS

Zell et al. "Efficient Hydrogen Liberation from Formic Acid Catalyzed by a Well-Defined Iron Pincer Complex under Mild Conditions." Chem. Eur. J. May 2013, 8068-8072.*
Cover sheet for Zell et al. "Efficient Hydrogen Liberation from Formic Acid Catalyzed by a Well-Defined Iron Pincer Complex under Mild Conditions." Chem. Eur. J. May 2013, 8068-8072.*
STIC non-patent literature search (Year: 2018).*
A.Boddien, et al.; "Iron-Catalyzed Hydrogen Production from Formic Acid"; J. Am. Chem. Soc., 2010, 132 (26), Jun. 15, 2010; pp. 8924-8934.
D. A. Bulushev, et al.; "Hydrogen from formic acid decomposition over Pd and Au catalysts"; Catalysis Today, Catalytic Surface Science, vol. 154, Issues 1-2, Sep. 1, 2010, pp. 7-12.
Y. Huang, et al.; "Novel PdAu@Au/C Core-Shell Catalyst: Superior Activity and Selectivity in Formic Acid Decomposition for Hydrogen Generation"; American Chemical Society, Chemistry of Materials, 2010, 22 (18), Aug. 25, 2010;pp. 5122-5128.
J. D. Scholten, et al.; "Decomposition of Formic Acid Catalyzed by a Phosphine-Free Ruthenium Complex in a Task-Specific Ionic Liquid"; CHEMCATCHEM, vol. 2, Issue 10; Oct. 11, 2010; pp. 1265-1270.
A. Majewski, et al.; "A continuous-Flow Method for the Generation of Hydrogen from Formic Acid"; ChemSusChem, vol. 3, Issue 4; Apr. 26, 2010; pp. 431-434.
Communication pursuant to Article 94(3) EPC in related European Patent Application No. 14841387.5, dated Feb. 21, 2018 (Reference D1 was provided in an IDS to the USPTO on Jun. 2, 2016).
Georgy A. Filonenko et al: "The impact of Metal-Ligan Cooperation in Hydrogenation of Carbon Dioxide Catalyzed by Ruthenium PNP Pincer", ACS Catalysis, vol. 3, No. 11, Oct. 4, 2013 (Oct. 4, 2013), pp. 2522-2526, XP055087151, ISSN: 2155-5435, DOI: 10.1021/cs4006869.
Li-Peng He et al: "Efficient transfer hydrogenation reaction Catalyzed by a dearomatized PN3P ruthenium pincer complex under base-free Conditions", Journal of Organometallic Chemistry, vol. 700, Mar. 1, 2012 (Mar. 1, 2012), pp. 202-203, XP055062858, ISSN: 0022-328X, DOI: 10.1016/j.jorganchem.2011.10.017.
Shunichi Fukuzum et al: "Unusually Large Tunneling Effect on Highly Efficient Generation of Hydrogen and Hydrogen Isotoped in pH-Selective Decomposition of Formic Acid Catalyzed by a Heterodinuclear Iridium-Ruthenium Complex in Water", Journal of the American Chemical Society, vol. 132, No. 5, Feb. 10, 2010 (Feb. 10, 2010), pp. 1496-1497, XP55160101, ISSN: 0002-7863, DOI: 10.1021/ja910349w.
First Office Action in related Chinese Application No. 2014800738983, dated May 29, 2018 (all references were previously cited in an IDS filed Jun. 2, 2016).
Examination Report No. 1 for Standard Patent Application in related Australian Application No. 2014358867, dated Aug. 7, 2017.

(Continued)

*Primary Examiner* — Paul A Wartalowicz
(74) *Attorney, Agent, or Firm* — Billion & Armitage; Lisbeth C. Robinson

(57) ABSTRACT

The invention describes phospho-amino pincer-type ligands, metal complexes thereof, and catalytic methods comprising such metal complexes.

21 Claims, 1 Drawing Sheet

(56) References Cited

OTHER PUBLICATIONS

International Preliminary Report on Patentability in related International Application No. PCT/IB2014/003120, dated Jun. 7, 2016.
International Search Report in related International Application No. PCT/IB2014/003120, dated May 8, 2015.
Written Opinion of the International Searching Authority in related International Application No. PCT/IB2014/003120, dated May 8, 2015.

* cited by examiner

TABLE 4

| Entry | T (°C) | P (psi)[c] | Time (h) | Yield (%)[d] | TON |
|---|---|---|---|---|---|
| 1[a] | 20 | 120 | 13 | 2.4 | 24 |
| 2[a] | 20 | 240 | 13 | 5.2 | 52 |
| 3[a] | 40 | 120 | 14 | 37.9 | 379 |
| 4[a] | 40 | 240 | 16 | 79.2 | 792 |
| 5[b] | 40 | 120 | 14 | 56.8 | 568 |
| 6[b] | 40 | 240 | 16 | 90.0 | 900 |

METAL-LIGAND COOPERATIVE CATALYSIS THROUGH N-H ARM DEPROTONATION/PYRIDINE DEAROMATIZTION FOR EFFICIENT HYDROGEN GENERATION FROM FORMIC ACID

CROSS REFERENCE TO RELATED APPLICATIONS

This application is a national phase application under 35 U.S.C. 371 of International Application No. PCT/IB2014/003120 filed Nov. 26, 2014, which claims the benefit of priority to U.S. Provisional Application Ser. No. 61/910,350, filed Dec. 2, 2013. The entire contents of each of the above-referenced disclosures are specifically incorporated herein by reference without disclaimer.

FIELD OF THE INVENTION

The present invention relates generally to the field of chemistry and catalysis. More particularly, it relates to phospho-amino pincer-type ligands, metal complexes thereof, and catalytic methods comprising such metal complexes.

BACKGROUND OF THE INVENTION

One of the most important challenges in the 21st century is energy. This involves the substantial transformation towards a clean energy system that meets our future needs without substantial damage to nature.[1,2] Hydrogen ($H_2$) is expected to play a crucial role as a secondary fuel and energy carrier in such a system.[3,4] $H_2$ has a high gravimetric energy density of 33.3 kW·h/kg and it can be converted into energy in an internal combustion engine or fuel cells with the production of water ($H_2O$) as the only "byproduct".[5] However, it is believed that the hydrogen economy will not occur until significant technological advances in $H_2$ production, storage and delivery systems are made.[6] Among these issues, $H_2$ storage has represented a great challenge. Conventional $H_2$ storage in high-pressure compressed gas cylinders or cryogenic liquid tanks is straight forward, but it suffers from high energy input and low volumetric energy capacity.[7] Alternative approaches through physical adsorption of $H_2$ in high-surface-area materials, such as metal-organic frameworks, zeolites, nanostructured carbon materials, etc., experience the limitation of temperature and pressure ranges.[8-10] While chemical hydride systems have high gravimetric $H_2$ capacities up to 20 wt %, the low reversibility prohibits their widespread applications.[11-13] In this regard, formic acid (FA) becomes an attractive choice. Although FA contains only 4.35 wt % of $H_2$, because of its high density of 1.22 g/cm$^3$, its volumetric capacity reaches 53.0 g $H_2$/L. This is equivalent to an energy density of 1.77 kW·h/L, suitable for automotive and mobile applications. A carbon neutral system for $H_2$ storage can be created when efficient hydrogenation of carbon dioxide ($CO_2$) to FA/formates and selective dehydrogenation of FA are developed.[14-17]

The decomposition of FA to $H_2$ and $CO_2$ is thermodynamically favored, but the energy barrier is high and the selectivity is low (for the formation of $H_2O$ and CO) in the absence of a suitable catalyst. After the potential of utilizing $CO_2$ as a $H_2$ storage material was recognized,[18,19] a number of homogeneous and heterogeneous catalyst systems have been developed recently for the generation of $H_2$ from FA.[20-43] Reactions give significantly enhanced turnover frequencies (TOFs) and turnover numbers (TONs) by using FA/NEt$_3$ azeotrope or FA/formate mixtures at the cost of decreasing the overall volumetric $H_2$ capacity. Only a few molecular catalysts show good activities in the absence of base additives.[25,32,43]

Therefore, a need exists for the development of novel catalyst systems that overcome one or more of the current disadvantages noted above.

BRIEF SUMMARY OF THE INVENTION

In one aspect, PN$^3$-pincer ligands are provided, with corresponding intermediates, and metal complexes thereof. These PN$^3$-pincer complexes have been found to convert formic acid to hydrogen and carbon dioxide, substantially without generation of carbon monoxide, more particularly without any detectable carbon monoxide, indicating that the purity of the regenerated gas is suitable for use in hydrogen fuel cells. Conversion of formic acid to hydrogen and carbon dioxide was effected under mild reaction conditions. In some aspects, the reactions were performed under base-free conditions. Additionally, the catalyst systems described herein can be used for the hydrogenation of carbon dioxide to formate or formic acid.

In one aspect, the present disclosure provides phospho-amino ligands and methods which include the use of the ligands and their complexes described herein to produce hydrogen from formic acid. The method includes the step of contacting formic acid with a complex comprising a ligand and a metal or metal ion, wherein the ligand is a compound according to formula (I), or a deprotonated version thereof, and the ligand is associated with the metal or metal ion, wherein formula (I) comprises:

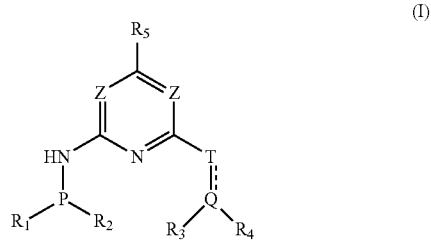

(I)

wherein $R_1$ and $R_2$, are each independently alkyl$_{(C\le12)}$, aryl$_{(C\le12)}$, aralkyl$_{(C\le12)}$, or a substituted version of any of these groups;
$R_3$, and $R_4$, if present, are each independently alkyl$_{(C\le12)}$, aryl$_{(C\le12)}$, aralkyl$_{(C\le12)}$, or a substituted version of any of these groups;
$R_5$ is a hydrogen atom or an alkyl$_{(C\le12)}$, aryl$_{(C\le12)}$, aralkyl$_{(C\le12)}$, amino, hydroxyl, alkoxyl or a substituted version of any of these groups;
each Z, independently, is CR$_6$, N or P;
$R_6$ is a hydrogen atom or an alkyl$_{(C\le12)}$, aryl$_{(C\le12)}$, aralkyl$_{(C\le12)}$, amino, hydroxyl, alkoxyl or a substituted version of any of these groups;
T is a N, NR$_7$, CR$_8$, or CR$_9$R$_{10}$;
$R_7$, $R_8$, $R_9$ and $R_{10}$ are each independently a hydrogen, alkyl$_{(C\le12)}$, aryl$_{(C\le12)}$, aralkyl$_{(C\le12)}$, or a substituted version of any of these groups;
Q is P or N;
optionally, wherein T and Q, together, form a 5 or 6 membered heterocyclic ring; wherein the heterocyclic ring can optionally be substituted with one or more heteroatoms and or one or more sites of the heterocyclic ring are substituted with one or more alkyl$_{(C\leq12)}$, aryl$_{(C\leq12)}$, aralkyl$_{(C\leq12)}$, or a substituted version of any of these groups, and optionally wherein the heterocyclic ring can have a fused ring attached thereto, provided when T and Q form a 5 or 6 membered heterocyclic ring, one or both of $R_3$ and/or $R_4$ are not present; and ===== designates a single bond or a double bond.

In another aspect, the method includes the step of contacting formic acid with a complex comprising formula (II):

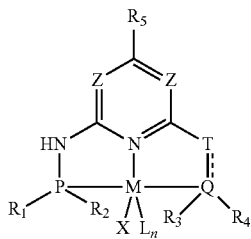

(II)

wherein $R_1$, $R_2$, $R_3$, $R_4$, $R_5$, Z, $R_6$, T, $R_7$, $R_8$, $R_9$, $R_{10}$, Q and ===== are as defined above, M is a metal or metal ion that is a group 8 metal or metal ion, L is a neutral or an anionic ligand, "n" is 0, 1 or 2 and X is a halide or a hydrogen atom In still another aspect, the method includes the step of contacting formic acid with a complex comprising formula (III):

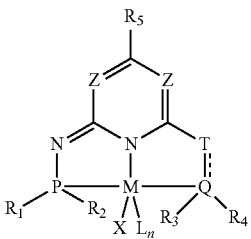

(III)

wherein $R_1$, $R_2$, $R_3$, $R_4$, $R_5$, Z, $R_6$, T, $R_7$, $R_8$, $R_9$, $R_{10}$, Q, and =====, L, n, M and X are as defined above.

In still another aspect, the method includes the step of contacting formic acid with a complex comprising formula (IV):

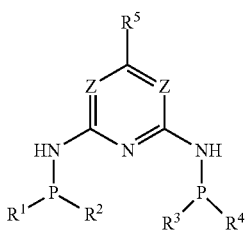

(IV)

wherein $R_1$, $R_2$, $R_3$, $R_4$, $R_5$, Z, $R_6$, are as defined above.

In another aspect, the method includes the step of contacting formic acid with a complex comprising formula (V):

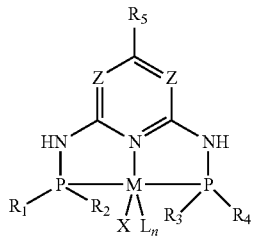

(V)

wherein $R_1$, $R_2$, $R_3$, $R_4$, $R_5$, Z, $R_6$, M, L, n and X are as defined above.

In yet another aspect, the method includes the step of contacting formic acid with a complex comprising formula (VI):

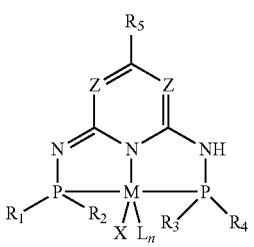

(VI)

wherein $R_1$, $R_2$, $R_3$, $R_4$, $R_5$, Z, $R_6$, M, L, n and X are as defined above.

In certain aspects for formulae (II), (III), (V) and (VI), X is H and L is CO (carbon monoxide) or vice versa.

In other aspects for formulae (II), (III), (V) and (VI), X and L cannot both be CO (carbon monoxide) or hydrogen. In other aspects, both X and L are hydrogen. In still other aspects, both X and L are CO.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 1 shows Table 4. [a] Catalyst C3 (1.0×10$^{-3}$ mmol) and KOH (1.0 mmol) in a mixture of 5.0 mL of toluene and 1.0 mL of H$_2$O. [b] Catalyst C3 (1.0×10$^{-3}$ mmol) and KOH (1.0 mmol) in a mixture of 1.0 mL of toluene and 5.0 mL of H$_2$O. [c] P$_{H2}$:P$_{CO2}$=1:1. [c] Yields of HCOOK were calculated based on $^1$H NMR analysis using sodium 3-(trimethylsilyl)-1-propanesulfonate as an internal standard.

DETAILED DESCRIPTION

In certain aspects of the present invention, there are provided a new class of pincer-type ligands, including those having a disubstituted-phosphinoamino (NH—PR$_2$) arm. Metal complexes of such ligands are also provided, including complexes that may be used as catalysts for a variety of transformations, including conversion of formic acid to carbon dioxide and hydrogen or hydrogenation of carbon dioxide to form a formate or formic acid. Upon complexation of ligands described herein to a transition metal and treatment of a base, in some embodiments, the resulting complex can undergo dearomatization after the elimination of H-X.

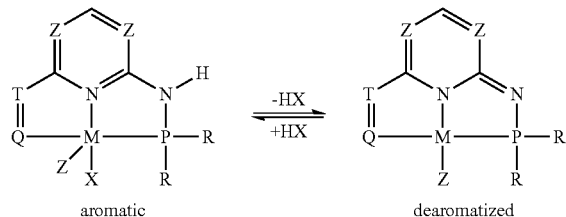

aromatic    dearomatized wherein T, Q and Z are as described herein.

In one aspect, the present disclosure provides phosphoamino ligands and methods which include the use of the ligands and their complexes described herein to produce hydrogen from formic acid. The method includes the step of contacting formic acid with a complex comprising a ligand and a metal or metal ion, wherein the ligand is a compound according to formula (I), or a deprotonated version thereof, and the ligand is associated with the metal or metal ion, wherein formula (I) comprises:

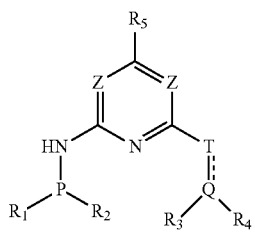

(I)

wherein $R_1$ and $R_2$, are each independently alkyl$_{(C \leq 12)}$, aryl$_{(C \leq 12)}$, aralkyl$_{(C \leq 12)}$, or a substituted version of any of these groups;
$R_3$, and $R_4$, if present, are each independently alkyl$_{(C \leq 12)}$, aryl$_{(C \leq 12)}$, aralkyl$_{(C \leq 12)}$, or a substituted version of any of these groups;
$R_5$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;
each Z, independently, is CR$_6$, N or P;
$R_6$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;
T is a N, NR$_7$, CR$_8$, or CR$_9$R$_{10}$;
$R_7$, $R_8$, $R_9$ and $R_{10}$ are each independently a hydrogen, alkyl$_{(C \leq 12)}$, aryl$_{(C \leq 12)}$, aralkyl$_{(C \leq 12)}$, or a substituted version of any of these groups;
Q is P or N;
optionally, wherein T and Q, together, form a 5 or 6 membered heterocyclic ring; wherein the heterocyclic ring can optionally be substituted with one or more heteroatoms and or one or more sites of the heterocyclic ring are substituted with one or more alkyl$_{(C \leq 12)}$, aryl$_{(C \leq 12)}$, aralkyl$_{(C \leq 12)}$, or a substituted version of any of these groups, and optionally wherein the heterocyclic ring can have a fused ring attached thereto, provided when T and Q form a 5 or 6 membered heterocyclic ring, $R_3$ and $R_4$ are not present; and
------ designates a single bond or a double bond.

In another aspect, the method includes the step of contacting formic acid with a complex comprising formula (II):

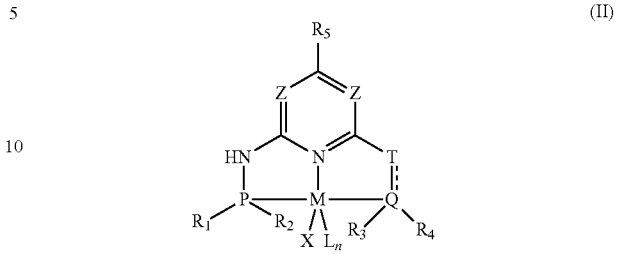

(II)

wherein $R_1$, $R_2$, $R_3$, $R_4$, $R_5$, Z, $R_6$, T, $R_7$, $R_8$, $R_9$, $R_{10}$, Q and ------ are as defined above, M is a metal or metal ion that is a group 8 metal or metal ion, L is a neutral or an anionic ligand, "n" is 0, 1 or 2 and X is a halide or a hydrogen atom In still another aspect, the method includes the step of contacting formic acid with a complex comprising formula (III):

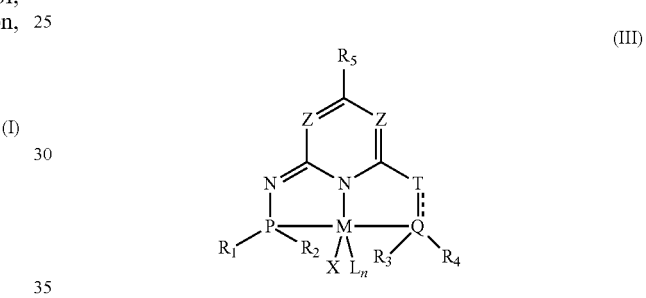

(III)

wherein $R_1$, $R_2$, $R_3$, $R_4$, $R_5$, Z, $R_6$, T, $R_7$, $R_8$, $R_9$, $R_{10}$, Q, and ------, L, n, M and X are as defined above.

In still another aspect, the method includes the step of contacting formic acid with a complex comprising formula (IV):

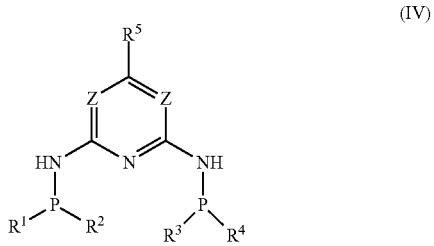

(IV)

wherein $R_1$, $R_2$, $R_3$, $R_4$, $R_5$, Z, $R_6$, are as defined above.

In another aspect, the method includes the step of contacting formic acid with a complex comprising formula (V):

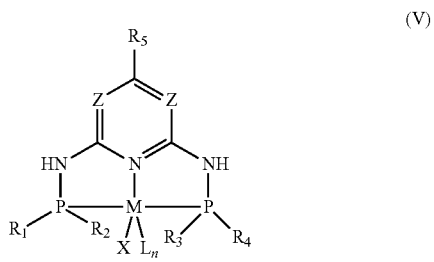

(V)

wherein $R_1$, $R_2$, $R_3$, $R_4$, $R_5$, $Z$, $R_6$, $M$, $L$, n and $X$ are as defined above.

In yet another aspect, the method includes the step of contacting formic acid with a complex comprising formula (VI):

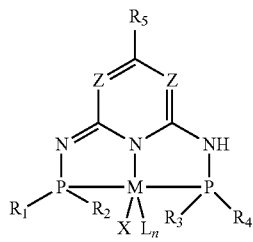

(VI)

wherein $R_1$, $R_2$, $R_3$, $R_4$, $R_5$, $Z$, $R_6$, $M$, $L$, n and $X$ are as defined above.

In certain aspects for formulae (II), (III), (V) and (VI), X is a hydride (H) or CO and L is CO (carbon monoxide) or H.

In other aspects for formulae (II), (III), (V) and (VI), X and L cannot both be CO (carbon monoxide) or hydrogen.

M is a transition metal or a transition metal ion including iron (Fe), ruthenium (Ru), Osmium (Os) and hassium (Hs).

L is a neutral or anionic ligand, such as carbon monoxide (C)), phosphine, CN, a hydride, H-BH$_3$, or a halide.

Halides, as noted herein, include, for example, chloride, bromide, iodide, or fluoride.

It should be understood that the dative bonds depicted with metal or metal ion "M" can be covalent, ionic, van der Waals type interactions, complexation interactions or other types of interactions where the metal (M). It should be understood that there is an association with the metal or metal ion and one or more of the nitrogen of the pyridine ring, the dearomatized N of the pyridine ring, a "P", a "T", an NH, an imine nitrogen, or "Q" of the ligands described herein. The stereochemistry of the "L" and or halide "X" associated with the metal or metal ion "M" is not limited to a planar structure but is merely depicted this way for convenience.

Selected structures include, for example, PN$^3$-pincer ruthenium (Ru) complexes C1 through C3, which are useful for dehydrogenation of formic acid are depicted below. Further details regarding different embodiments are provided throughout this disclosure.

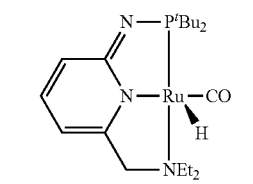

C1

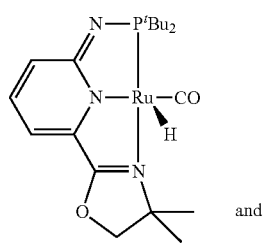

C2 and

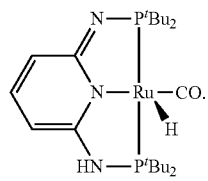

C3

Phospho-Amino Pincer-Type Ligands

In one aspect, the disclosure provides compounds of formula (IV)

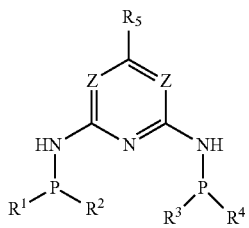

(IV)

wherein $R_1$, $R_2$, $R_3$, and $R_4$ are each independently alkyl$_{(C \le 12)}$, aryl$_{(C \le 12)}$, aralkyl$_{(C \le 12)}$, or a substituted version of any of these groups;

$R_5$ is a hydrogen atom or an alkyl$_{(C \le 12)}$, aryl$_{(C \le 12)}$, aralkyl$_{(C \le 12)}$, or a substituted version of any of these groups;

each Z, independently, is CR$_6$, N or P;

$R_6$ is a hydrogen atom or an alkyl$_{(C \le 12)}$, aryl$_{(C \le 12)}$, aralkyl$_{(C \le 12)}$, amino, hydroxyl, alkoxyl or a substituted version of any of these groups; and provided that when $R^1$, $R^2$, $R^3$ and $R^4$ are t-butyl groups, $R_5$ is not a hydrogen atom and each Z is not CH, when $R^1$, $R^2$, $R^3$ and $R^4$ are isopropyl groups, $R_5$ is not a phenyl group and each Z is not N and when $R_1$, $R_2$, $R_3$, and $R_4$ are phenyl, $R_5$ is not a hydrogen atom and each Z is not CH.

Examples of such ligands and methods of preparing them, and optionally deprotonating them, are provided throughout this disclosure. For example, see He, L.-P.; Chen, T.; Gong, D.; Lai, Z.-P.; Huang, K.-W. *Organometallics* 2012, 31, 5208-5211. C2. Chen, T.; He, L.; Gong, D.; Yang, L.; Maio, X.; Eppinger, J.; Huang, K.-W. *Tetrahedron Lett.* 2012, 53, 4409-4412. C3. He, L.-P.; Chen, T.; Xue, D.; Eddaoudi, M.; Huang, K.-W. *J. Organomet. Chem.* 2012, 700, 202-206, the contents of which are incorporated herein in their entirety.

These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein. The above methods can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein.

Phospho-Amino, Pincer-Type Ligand Complexes and Methods of Use

The present disclosure also provides metal complexes of this novel class of ligands. Such complexes may be used to facilitate a variety of organic transformations, including conversion of formic acid to hydrogen and carbon dioxide and or hydrogenation of carbon dioxide to form a formate or formic acid.

For example, ruthenium complexes of ligands can be made, and optionally deprotonated, to provide a dearomatized pyridine moiety and an imine arm. Ruthenium complexes of ligands C1, C2 and C3 can catalyze, for example, the conversion of formic acid to hydrogen and carbon dioxide (without any generation of carbon monoxide) (Tables 1, 2 and 3) and hydrogenation of carbon dioxide to formate (Table 4).

The above methods can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein.

Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "sulfinyl" means —S(O)— (see below for definitions of groups containing the term sulfinyl, e.g., alkylsulfinyl).

In the context of chemical formulas, the symbol "—" means a single bond, "=" means a double bond, and "≡" means triple bond. The symbol " ---- " represents an optional bond, which if present is either single or double. The symbol "====" represents a single bond or a double bond. Thus, for example, the structure

includes the structures

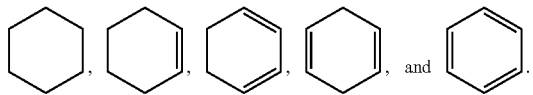

As will be understood by a person of skill in the art, no one such ring atom forms part of more than one double bond. The symbol "◄■", when drawn perpendicularly across a bond indicates a point of attachment of the group. It is noted that the point of attachment is typically only identified in this manner for larger groups in order to assist the reader in rapidly and unambiguously identifying a point of attachment. The symbol "⦚⦚⦚⦚" means a single bond where the group attached to the thick end of the wedge is "out of the page." The symbol "∿∿∿" means a single bond where the group attached to the thick end of the wedge is "into the page". The symbol "∿∿∿" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

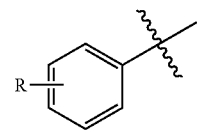

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

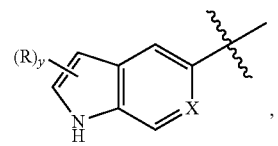

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system. For the groups and classes below, the following parenthetical subscripts further define the group/class as follows: "(Cn)" defines the exact number (n) of carbon atoms in the group/class. "(Cn)" defines the maximum number (n) of carbon atoms that can be in the group/class, with the minimum number as small as possible for the group in question, e.g., it is understood that the minimum number of carbon atoms in the group "alkenyl$_{(C\le8)}$" or the class "alkene$_{(C\le8)}$" is two. For example, "alkoxy$_{(C\le10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkanes/alkenyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$—(methylene), —CH$_2$CH$_2$—, —CH$_2$C(CH$_3$)$_2$CH$_2$—, —CH$_2$CH$_2$CH$_2$—, and

, are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

, are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one carbon-carbon triple bond, and no atoms other than carbon and hydrogen. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O) NH$_2$ or —OC(O)CH$_3$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or not fused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

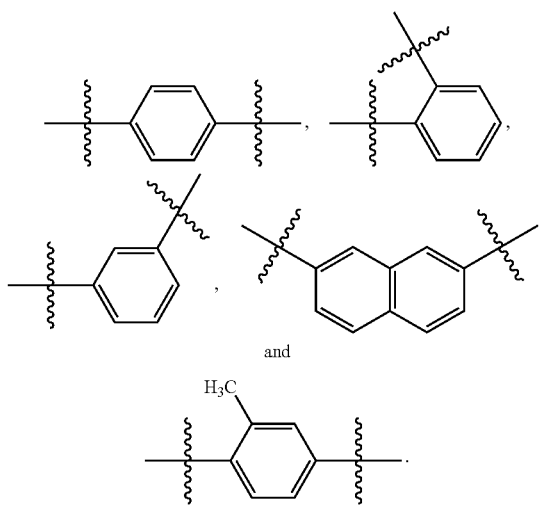

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

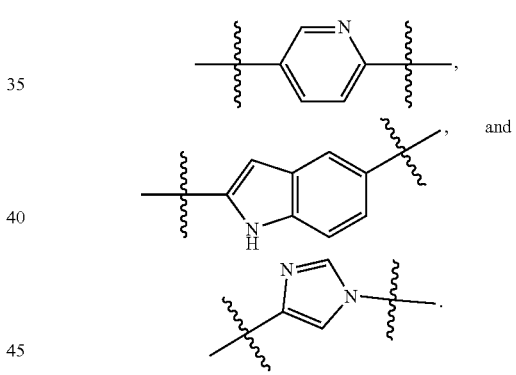

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —O—OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups —NHC(O)OCH$_3$ and —NHC(O)NHCH$_3$ are non-limiting examples of substituted amido groups.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following paragraphs enumerated consecutively from 1 through 51 provide for various aspects of the embodiments described herein. In one embodiment, in a first paragraph (1), the present invention provides a method to produce hydrogen from formic acid comprising the step of contacting formic acid with a complex comprising a ligand and a metal or metal ion, wherein the ligand is a compound according to formula (I), or a deprotonated version thereof, and the ligand is associated with the metal or metal ion, wherein formula (I) comprises:

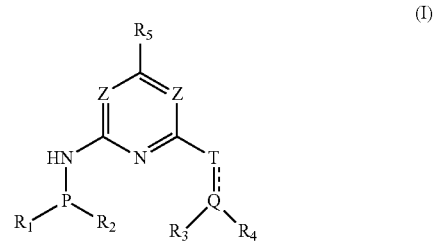

(I)

wherein R$_1$ and R$_2$, are each independently alkyl$_{(C \leq 12)}$, aryl$_{(C \leq 12)}$, aralkyl$_{(C \leq 12)}$, or a substituted version of any of these groups;

R$_3$, and R$_4$, if present, are each independently alkyl$_{(C \leq 12)}$, aryl$_{(C \leq 12)}$, aralkyl$_{(C \leq 12)}$, or a substituted version of any of these groups;

R$_5$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;

each Z, independently, is CR$_6$, N or P;

R$_6$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;

T is a N, NR$_7$, CR$_8$, or CR$_9$R$_{10}$;

R$_7$, R$_8$, R$_9$ and R$_{10}$ are each independently a hydrogen, alkyl$_{(C \leq 12)}$, aryl$_{(C \leq 12)}$, aralkyl$_{(C \leq 12)}$, or a substituted version of any of these groups;

Q is P or N;

optionally, wherein T and Q, together, form a 5 or 6 membered heterocyclic ring; wherein the heterocyclic ring can optionally be substituted with one or more heteroatoms and or one or more sites of the heterocyclic ring are substituted with one or more alkyl$_{(C\leq12)}$, aryl$_{(C\leq12)}$, aralkyl$_{(C\leq12)}$, or a substituted version of any of these groups, and optionally wherein the heterocyclic ring can have a fused ring attached thereto, provided when T and Q form a 5 or 6 membered heterocyclic ring, R$_3$ and R$_4$ are not present; and ------ designates a single bond or a double bond.

2. The method of paragraph 1, wherein T is NH and Q is P.

3. The method of paragraph 2, wherein R$_1$, R$_2$, R$_3$ and R$_4$ are each an alkyl$_{(C\leq12)}$.

4. The method of paragraph 3, wherein R$_1$, R$_2$, R$_3$ and R$_4$ are each a t-butyl group.

5. The method of paragraph 1, wherein T is CH$_2$ and Q is N.

6. The method of paragraph 5, wherein R$_1$, R$_2$, R$_3$ and R$_4$ are each an alkyl$_{(C\leq12)}$.

7. The method of paragraph 6, wherein R$_1$, and R$_2$ are t-butyl group and R$_3$ and R$_4$ are ethyl groups.

8. The method of paragraph 1, wherein T is C, Q is N and T and Q form

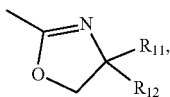

wherein R$_{11}$ and R$_{12}$, each independently, are a hydrogen atom or alkyl$_{(C\leq12)}$, aryl$_{(C\leq12)}$, aralkyl$_{(C\leq12)}$, or a substituted version of any of these groups.

9. The method of paragraph 8, wherein R$_{11}$ and R$_{12}$ are both methyl groups.

10. The method of any of paragraphs 1 through 9, wherein the metal or metal ion is a Group 8 metal or metal ion.

11. The method of any of paragraphs 1 through 10, wherein the metal or metal ion is based on ruthenium.

12. The method of any of paragraphs 1 through 11, wherein the complex further comprises a second ligand, wherein the second ligand is a halide or a hydrogen atom.

13. The method of paragraph 12, wherein the halide is chloride.

14. The method of paragraphs 12 or 13, wherein the complex further comprises a third ligand, wherein the third ligand is carbon monoxide.

15. The method of any of paragraphs 1 through 14, wherein the method produces carbon dioxide.

16. The method of any of paragraphs 1 through 15, wherein substantially no carbon monoxide is produced.

17. The method of paragraph 16, wherein no carbon monoxide is produced.

18. The method of any of paragraphs 1 through 17, wherein a polar aprotic solvent is present, such as DMSO.

19. The method of any of paragraphs 1 through 18, wherein the catalyst has a turnover number from about 500 to about 500,000.

20. A method to produce hydrogen from formic acid comprising the step of contacting formic acid with a compound of formula (II):

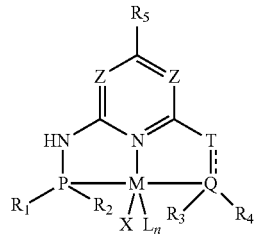

wherein R$_1$ and R$_2$, are each independently alkyl$_{(C\leq12)}$, aryl$_{(C\leq12)}$, aralkyl$_{(C\leq12)}$, or a substituted version of any of these groups;

R$_3$, and R$_4$, if present, are each independently alkyl$_{(C\leq12)}$, aryl$_{(C\leq12)}$, aralkyl$_{(C\leq12)}$, or a substituted version of any of these groups;

R$_5$ is a hydrogen atom or an alkyl$_{(C\leq12)}$, aryl$_{(C\leq12)}$, aralkyl$_{(C\leq12)}$, or a substituted version of any of these groups;

each Z, independently, is CR$_6$, N or P;

R$_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

M is a metal or metal ion that is a group 8 metal or metal ion;

L is a neutral or an anionic ligand;

n is 0, 1 or 2

X is a halide or a hydrogen atom;

T is a N, NR$_7$, CR$_8$, or CR$_9$R$_{10}$;

R$_7$, R$_8$, R$_9$ and R$_{10}$ are each independently a hydrogen, alkyl$_{(C\leq12)}$, aryl$_{(C\leq12)}$, aralkyl$_{(C\leq12)}$, or a substituted version of any of these groups;

Q is P or N;

optionally, wherein T and Q, together, form a 5 or 6 membered heterocyclic ring; wherein the heterocyclic ring can optionally be substituted with one or more heteroatoms and or one or more sites of the heterocyclic ring are substituted with one alkyl$_{(C\leq12)}$, aryl$_{(C\leq12)}$, aralkyl$_{(C\leq12)}$, or a substituted version of any of these groups, and optionally wherein the heterocyclic ring can have a fused ring attached thereto, provided when T and Q form a 5 or 6 membered heterocyclic ring, R$_3$ and R$_4$ are not present; and ------ designates a single bond or a double bond.

21. The method of paragraph 20, wherein T is NH and Q is P.

22. The method of paragraph 21, wherein R$_1$, R$_2$, R$_3$ and R$_4$ are each an alkyl$_{(C\leq12)}$.

23. The method of paragraph 22, wherein R$_1$, R$_2$, R$_3$ and R$_4$ are each a t-butyl group.

24. The method of paragraph 20, wherein T is CH$_2$ and Q is N.

25. The method of paragraph 24, wherein R$_1$, R$_2$, R$_3$ and R$_4$ are each an alkyl$_{(C\leq12)}$.

26. The method of paragraph 25, wherein R$_1$, and R$_2$ are t-butyl group and R$_3$ and R$_4$ are ethyl groups.

27. The method of paragraph 20, wherein T is C, Q is N and T and Q form

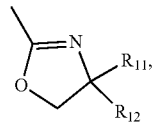

wherein $R_{11}$ and $R_{12}$, each independently, are a hydrogen atom or alkyl$_{(C≤12)}$, aryl$_{(C≤12)}$, aralkyl$_{(C≤12)}$, or a substituted version of any of these groups.

28. The method of paragraph 27, wherein $R_{11}$ and $R_{12}$ are both methyl groups.

29. The method of any of paragraphs 20 through 28, wherein the metal or metal ion is based on ruthenium.

30. The method of any of paragraphs 20 through 29, wherein X is chloride.

31. The method of any of paragraphs 20 through 30, wherein the method produces carbon dioxide.

32. The method of any of paragraphs 20 through 30, wherein substantially no carbon monoxide is produced.

33. The method of paragraph 32, wherein no carbon monoxide is produced.

34. The method of any of paragraphs 20 through 33, wherein a polar aprotic solvent is present, such as DMSO.

35. The method of any of paragraphs 20 through 34, wherein the catalyst has a turnover number from about 500 to about 500,000.

36. A method to produce hydrogen from formic acid comprising the step of contacting formic acid with a compound of formula (III):

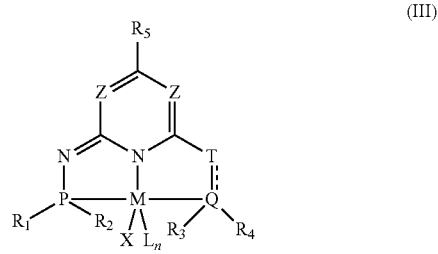

(III)

wherein $R_1$ and $R_2$, are each independently alkyl$_{(C≤12)}$, aryl$_{(C≤12)}$, aralkyl$_{(C≤12)}$, or a substituted version of any of these groups;
$R_3$, and $R_4$, if present, are each independently alkyl$_{(C≤12)}$, aryl$_{(C≤12)}$, aralkyl$_{(C≤12)}$, or a substituted version of any of these groups;
$R_5$ is a hydrogen atom or an alkyl$_{(C≤12)}$, aryl$_{(C≤12)}$, aralkyl$_{(C≤12)}$, or a substituted version of any of these groups;
each Z, independently, is $CR_6$, N or P;
$R_6$ is a hydrogen atom or an alkyl$_{(C≤12)}$, aryl$_{(C≤12)}$, aralkyl$_{(C≤12)}$, amino, hydroxyl, alkoxyl or a substituted version of any of these groups;
T is a N, $NR_7$, $CR_8$, or $CR_9R_{10}$;
$R_7$, $R_8$, $R_9$ and $R_{10}$ are each independently a hydrogen, alkyl$_{(C≤12)}$, aryl$_{(C≤12)}$, aralkyl$_{(C≤12)}$, or a substituted version of any of these groups;
Q is P or N;
M is a metal or metal ion that is a group 8 metal or metal ion;
L is a neutral or an anionic ligand;
n is 0, 1 or 2
X is a halide or a hydrogen atom; and
optionally, wherein T and Q, together, form a 5 or 6 membered heterocyclic ring; wherein the heterocyclic ring can optionally be substituted with one or more heteroatoms and or one or more sites of the heterocyclic ring are substituted with one alkyl$_{(C≤12)}$, aryl$_{(C≤12)}$, aralkyl$_{(C≤12)}$), or a substituted version of any of these groups, and optionally wherein the heterocyclic ring can have a fused ring attached thereto, provided when T and Q form a 5 or 6 membered heterocyclic ring, $R_3$ and $R_4$ are not present; and ------ designates a single bond or a double bond.

37. The method of paragraph 36, wherein T is NH and Q is P.

38. The method of paragraph 37, wherein $R_1$, $R_2$, $R_3$ and $R_4$ are each an alkyl$_{(C≤12)}$.

39. The method of paragraph 38, wherein $R_1$, $R_2$, $R_3$ and $R_4$ are each a t-butyl group.

40. The method of paragraph 36, wherein T is $CH_2$ and Q is N.

41. The method of paragraph 40, wherein $R_1$, $R_2$, $R_3$ and $R_4$ are each an alkyl$_{(C≤12)}$.

42. The method of paragraph 41, wherein $R_1$, and $R_2$ are t-butyl group and $R_3$ and $R_4$ are ethyl groups.

43. The method of paragraph 36, wherein T is C, Q is N and T and Q form

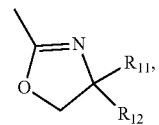

wherein $R_{11}$ and $R_{12}$, each independently, are a hydrogen atom or alkyl$_{(C≤12)}$, aryl$_{(C≤12)}$, aralkyl$_{(C≤12)}$, or a substituted version of any of these groups.

44. The method of paragraph 43, wherein $R_{11}$ and $R_{12}$ are both methyl groups.

45. The method of any of paragraphs 36 through 44, wherein the metal or metal ion is based on ruthenium.

46. The method of any of paragraphs 36 through 45, wherein X is chloride.

47. The method of any of paragraphs 36 through 46, wherein the method produces carbon dioxide.

48. The method of any of paragraphs 36 through 46, wherein substantially no carbon monoxide is produced.

49. The method of paragraph 48, wherein no carbon monoxide is produced.

50. The method of any of paragraphs 36 through 49, wherein a polar aprotic solvent is present, such as DMSO.

51. The method of any of paragraphs 36 through 50, wherein the catalyst has a turnover number from about 500 to about 500,000

The following paragraphs enumerated consecutively from 1 through 29 provide for aspects of the embodiments described herein. In one embodiment, in a first paragraph (1), the present invention provides a composition comprising a compound of formula (IV):

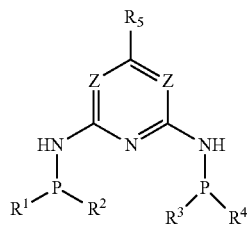

(IV)

wherein $R_1$, $R_2$, $R_3$, and $R_4$ are each independently alkyl$_{(C≤12)}$, aryl$_{(C≤12)}$, aralkyl$_{(C≤12)}$, or a substituted version of any of these groups;
$R_5$ is a hydrogen atom or an alkyl$_{(C≤12)}$, aryl$_{(C≤12)}$, aralkyl$_{(C≤12)}$, or a substituted version of any of these groups;
each Z, independently, is $CR_6$, N or P;

$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups; and provided that when $R^1$, $R^2$, $R^3$ and $R^4$ are t-butyl groups, $R_5$ is not a hydrogen atom and each Z is not CH, when $R^1$, $R^2$, $R^3$ and $R^4$ are isopropyl groups, $R_5$ is not a phenyl group and each Z is not N and when $R_1$, $R_2$, $R_3$, and $R_4$ are phenyl, $R_5$ is not a hydrogen atom and each Z is not CH.

2. The composition of paragraph 1, wherein $R_1$, $R_2$, $R_3$, and $R_4$ are each isopropyl groups, each Z is CH and $R_5$ is a hydrogen atom.

3. A composition comprising a compound of formula (V):

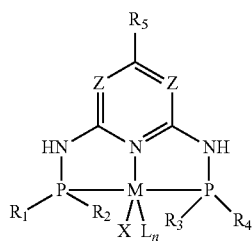

(V)

wherein $R_1$, $R_2$, $R_3$, and $R_4$ are each independently alkyl$_{(C\leq12)}$, aryl$_{(C\leq12)}$, aralkyl$_{(C\leq12)}$, or a substituted version of any of these groups;

$R_5$ is a hydrogen atom or an alkyl$_{(C\leq12)}$, aryl$_{(C\leq12)}$, aralkyl$_{(C\leq12)}$, or a substituted version of any of these groups;

each Z, independently, is $CR_6$, N or P;

$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

M is a metal or metal ion that is a group 8 metal or metal ion;

L is a neutral or an anionic ligand;

n is 0, 1 or 2;

X is a halide or a hydrogen atom; and provided that when $R^1$, $R^2$, $R^3$ and $R^4$ are t-butyl groups, $R_5$ is not a hydrogen atom and each Z is not CH and when $R^1$, $R^2$, $R^3$ and $R^4$ are isopropyl groups, $R_5$ is not a phenyl group and each Z is not N.

4. The composition of paragraph 3, wherein $R_1$, $R_2$, $R_3$, and $R_4$ are each isopropyl groups, each Z is CH and $R_5$ is a hydrogen atom.

5. A composition comprising a compound of formula (VI):

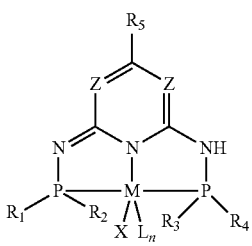

(VI)

wherein $R_1$, $R_2$, $R_3$, and $R_4$ are each independently alkyl$_{(C\leq12)}$, aryl$_{(C\leq12)}$, aralkyl$_{(C\leq12)}$, or a substituted version of any of these groups;

$R_5$ is a hydrogen atom or an alkyl$_{(C\leq12)}$, aryl$_{(C\leq12)}$, aralkyl$_{(C\leq12)}$, or a substituted version of any of these groups;

each Z, independently, is $CR_6$, N or P;

$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

M is a metal or metal ion that is a group 8 metal or metal ion;

L is a neutral or an anionic ligand;

n is 0, 1 or 2;

X is a halide or a hydrogen atom; and provided that when $R^1$, $R^2$, $R^3$ and $R^4$ are t-butyl groups, $R_5$ is not a hydrogen atom, each Z is not CH and M is not Ru, and when $R^1$, $R^2$, $R^3$ and $R^4$ are isopropyl groups, $R_5$ is not a phenyl group, each Z is not N and M is not Ir.

6. The composition of paragraph 5, wherein $R_1$, $R_2$, $R_3$, and $R_4$ are each isopropyl groups, each Z is CH and $R_5$ is a hydrogen atom.

7. A complex comprising a ligand and a metal or metal ion, wherein the ligand is a compound according to paragraph 1, or a deprotonated version thereof, and the ligand is associated with the metal or metal ion, provided that $R^1$, $R^2$, $R^3$ and $R^4$ are t-butyl groups, $R_5$ is not a hydrogen atom, each Z is not CH and M is not Ru, and when $R^1$, $R^2$, $R^3$ and $R^4$ are isopropyl groups, $R_5$ is not a phenyl group, each Z is not N and M is not Ir.

8. The complex of paragraph 7, wherein the metal or metal ion is a group 8 metal or metal ion.

9. The complex of paragraph 8, wherein the metal or metal ion is based on ruthenium.

10. The complex according to paragraph 7, wherein the complex further comprises a second ligand, wherein the second ligand is chloride.

11. The complex according to paragraph 10, wherein the complex further comprises a third ligand, wherein the third ligand is carbon monoxide.

12. A method to produce hydrogen from formic acid comprising the step of contacting formic acid with a compound of formula (V):

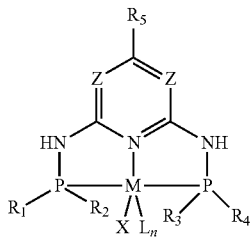

(V)

wherein $R_1$, $R_2$, $R_3$, and $R_4$ are each independently alkyl$_{(C\leq12)}$, aryl$_{(C\leq12)}$, aralkyl$_{(C\leq12)}$, or a substituted version of any of these groups;

$R_5$ is a hydrogen atom or an alkyl$_{(C\leq12)}$, aryl$_{(C\leq12)}$, aralkyl$_{(C\leq12)}$, or a substituted version of any of these groups;

each Z, independently, is $CR_6$, N or P;

$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;

M is a metal or metal ion that is a group 8 metal or metal ion;

L is a neutral or an anionic ligand;

n is 0, 1 or 2; and

X is a halide or a hydrogen atom.

13. The method of paragraph 12, wherein the method produces carbon dioxide.

14. The method of paragraph 12 or 13, wherein substantially no carbon monoxide is produced.

15. The method of paragraph 12 or 13, wherein no carbon monoxide is produced.

16. The method of any of paragraphs 12 through 15, wherein a polar aprotic solvent is present, such as DMSO.

17. The method of any of paragraphs 12 through 15, wherein the catalyst has a turnover number from about 500 to about 500,000.

18. A method to produce hydrogen from formic acid comprising the step of contacting formic acid with a compound of formula (VI):

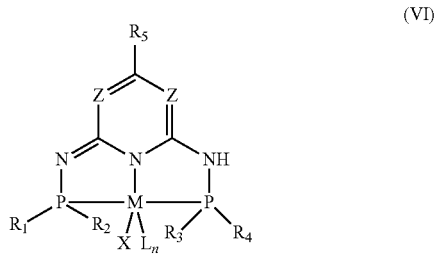

(VI)

wherein $R_1$, $R_2$, $R_3$, and $R_4$ are each independently alkyl$_{(C\leq12)}$, aryl$_{(C\leq12)}$, aralkyl$_{(C\leq12)}$, or a substituted version of any of these groups;
$R_5$ is a hydrogen atom or an alkyl$_{(C\leq12)}$, aryl$_{(C\leq12)}$, aralkyl$_{(C\leq12)}$, or a substituted version of any of these groups;
each Z, independently, is $CR_6$, N or P;
$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;
M is a metal or metal ion that is a group 8 metal or metal ion;
L is a neutral or an anionic ligand;
n is 0, 1 or 2; and
X is a halide or a hydrogen atom.

19. The method of paragraph 18, wherein the method produces carbon dioxide.

20. The method of paragraph 18 or 19, wherein substantially no carbon monoxide is produced.

21. The method of paragraph 18 or 19, wherein no carbon monoxide is produced.

22. The method of any of paragraphs 18 through 21, wherein a polar aprotic solvent is present, such as DMSO.

23. The method of any of paragraphs 18 through 21, wherein the catalyst has a turnover number from about 500 to about 500,000.

24. A method to produce hydrogen from formic acid comprising the step of contacting formic acid with a complex comprising a ligand and a metal or metal ion, wherein the ligand is a compound according to formula (IV), or a deprotonated version thereof, and the ligand is associated with the metal or metal ion, wherein formula (IV) comprises:

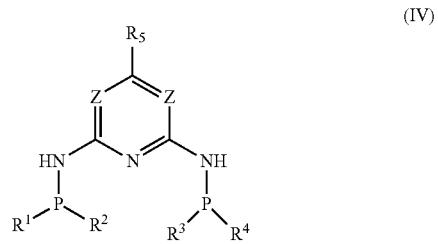

(IV)

wherein $R_1$, $R_2$, $R_3$, and $R_4$ are each independently alkyl$_{(C\leq12)}$, aryl$_{(C\leq12)}$, aralkyl$_{(C\leq12)}$, or a substituted version of any of these groups;
$R_5$ is a hydrogen atom or an alkyl$_{(C\leq12)}$, aryl$_{(C\leq12)}$, aralkyl$_{(C\leq12)}$), or a substituted version of any of these groups;
each Z, independently, is $CR_6$, N or P; and
$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups.

25. The method of paragraph 24, wherein the method produces carbon dioxide.

26. The method of paragraph 24 or 25, wherein substantially no carbon monoxide is produced.

27. The method of paragraph 24 or 25, wherein no carbon monoxide is produced.

28. The method of any of paragraphs 24 through 27, wherein a polar aprotic solvent is present, such as DMSO.

29. The method of any of paragraphs 25 through 27, wherein the catalyst has a turnover number from about 500 to about 500,000

In another aspect, method to produce formic acid or a formate is provided comprising the step of contacting carbon dioxide and hydrogen under increased pressure relative to atmospheric pressure, with a complex comprising a ligand and a metal or metal ion, wherein the ligand is a compound according to formula (I), or a deprotonated version thereof, and the ligand is associated with the metal or metal ion, wherein formula (I) comprises:

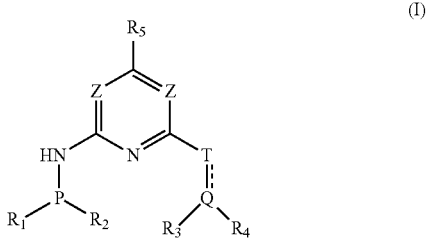

(I)

wherein $R_1$ and $R_2$, are each independently alkyl$_{(C\leq12)}$, aryl$_{(C\leq12)}$, aralkyl$_{(C\leq12)}$, or a substituted version of any of these groups;
$R_3$, and $R_4$, if present, are each independently alkyl$_{(C\leq12)}$, aryl$_{(C\leq12)}$, aralkyl$_{(C\leq12)}$, or a substituted version of any of these groups;
$R_5$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;
each Z, independently, is $CR_6$, N or P;
$R_6$ is a hydrogen atom or an alkyl$_{(C\leq12)}$, aryl$_{(C\leq12)}$, aralkyl$_{(C\leq12)}$, amino, hydroxyl, alkoxyl or a substituted version of any of these groups;
T is a N, $NR_7$, $CR_8$, or $CR_9R_{10}$;
$R_7$, $R_8$, $R_9$ and $R_{10}$ are each independently a hydrogen, alkyl$_{(C\leq12)}$, aryl$_{(C\leq12)}$, aralkyl$_{(C\leq12)}$, or a substituted version of any of these groups;
Q is P or N;
optionally, wherein T and Q, together, form a 5 or 6 membered heterocyclic ring; wherein the heterocyclic ring can optionally be substituted with one or more heteroatoms and or one or more sites of the heterocyclic ring are substituted with one or more alkyl$_{(C\leq12)}$, aryl$_{(C\leq12)}$, aralkyl$_{(C\leq12)}$, or a substituted version of any of these groups, and optionally wherein the heterocyclic ring can have a fused ring attached thereto, provided when T and Q form a 5 or 6 membered heterocyclic ring, $R_3$ and $R_4$ are not present; and ------ designates a single bond or a double bond, such that a formate or formic acid is produced.

In still another aspect, a method is provided to produce formic acid or a formate, comprising the step of contacting carbon dioxide and hydrogen under increased pressure relative to atmospheric pressure with a complex comprising a ligand and a metal or metal ion, wherein the ligand is a compound according to formula (IV), or a deprotonated version thereof, and the ligand is associated with the metal or metal ion, wherein formula (IV) comprises:

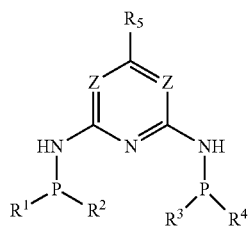

(IV)

wherein $R_1$, $R_2$, $R_3$, and $R_4$ are each independently alkyl$_{(C \leq 12)}$, aryl$_{(C \leq 12)}$, aralkyl$_{(C \leq 12)}$, or a substituted version of any of these groups;

$R_5$ is a hydrogen atom or an alkyl$_{(C \leq 12)}$, aryl$_{(C \leq 12)}$, aralkyl$_{(C \leq 12)}$, or a substituted version of any of these groups;

each Z, independently, is $CR_6$, N or P; and $R_6$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups, such that formic acid or a formate is produced.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Generally the ligands and complexes can be prepared by the methods described in U.S. patent Ser. No. 13/528,481, filed on Jun. 6, 2012, entitled "Phospho-amino Pincer-Type Ligands and Catalytic Metal Complexes Thereof", U.S. Provisional Patent Application No. 61/499,028, filed Jun. 20, 2011, and "Efficient transfer hydrogenation reation Catalyzed by a dearomatized PN$^3$P ruthenium pincer complex under base-free Conditions", Journal of Organometallic Chemistry, 700 (2012) 202-206, "A sustainable catalytic pyrrole synthesis", Nature Chemistry Vol. 5, 2013, 140-144 and Z. anorg. allg. Chem. 545 (1987) 83-97, the contents of which are incorporated herein by reference in their entirety.

Example 1 provides catalyzed production of hydrogen from formic acid. The reaction was conducted under air in a reaction flask. TON was calculated by the highest volume of hydrogen/formic acid consumed per weight of catalyst.

TABLE 1

Ru(II) pincer complexes catalyzed production of $H_2$ from formic acid.[a]

$$H-\overset{OH}{\underset{O}{C}} \xrightarrow{Cat.} H_2 + CO_2$$

| Entry | Solvent | Cat. | T (° C.) | TON |
|---|---|---|---|---|
| 1 | DMSO | C1 | 50 | 9800 |
| 2 | Toluene | C1 | 50 | — |
| 3 | DMSO | C2 | 50 | 2400 |
| 4 | Toluene | C2 | 50 | — |
| 5 | DMSO | C3 | 50 | 95000 |
| 6 | Toluene | C3 | 50 | 2000 |

[a]Reaction conditions: Ru catalyst (1.0 × 10$^{-3}$ mmol) and solvent (5.0 mL). Conversions were calculated by $H_2$ volumes with respect to the formic acid. Carbon dioxide was absorbed by an aqueous solution of potassium hydroxide.

TABLE 2

Effect of various solvents on the efficiency of formic acid dehydrogenation.[a]

| Entry | Solvent | T (°C.) | TON$_{1h}$ | TON |
|---|---|---|---|---|
| 1[b] | DMSO | 50 | 2380 | 95000 |
| 2 | CH$_3$CN | 50 | 1100 | 4800 |
| 3 | DMF | 50 | 900 | 3500 |
| 4 | Toluene | 50 | 440 | 2000 |
| 5 | thf | 50 | 890 | 3600 |
| 6[c] | thf/H$_2$O | 50 | 76.5 | 540 |

[a]Reaction conditions: catalyst C3 (1.0 × 10$^{-3}$ mmol), solvent (5.0 mL). Conversions were calculated by $H_2$ volumes. Carbon dioxide was absorbed by an aqueous solution of potassium hydroxide.
[b]Activity of C3 after exposure to air for one month.
[c]thf/H$_2$O (1:1) under air.

TABLE 3

Effect of base (NEt$_3$) on the efficiency of formic acid dehydrogenation.[a]

| Entry | Solvent | Additive | T (°C.) | TON$_{1h}$ | TON |
|---|---|---|---|---|---|
| 1 | DMSO | — | 50 | 2380 | 95,000 |
| 2[b] | DMSO | Et$_3$N | 50 | 38 000 | >420,000 |
| 3 | DMSO | — | 80 | 12 000 | 27,000 |
| 4[b] | DMSO | Et$_3$N | 80 | 80 000 | >160,0000 |

[a]Reaction conditions: complex C3 (1.0 × 10$^{-3}$ mmol), solvent (5.0 mL).
[b]Et$_3$N (10.0 mmol) was added.

Plausible Mechanism for Hydrogenation of $CO_2$ and production of $H_2$ from formic acid using Ru(II)-pincer complex 3.

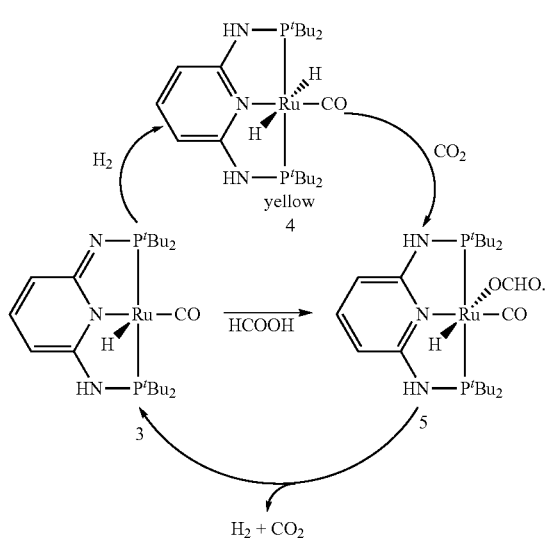

Table 4. Hydrogenation of Carbon Dioxide to formate Catalyzed by complex 3 (FIG. 1).

Not to be limited by theory, it is believed that the reaction proceeds by an increase in pressure in a system wherein carbon dioxide and or hydrogen are present. The pressure can be greater than 1 psi, particularly from about 10 to 500 psi, more particularly from about 100 to about 300 psi, and even more particularly from about 120 to about 240 psi. Inclusion of an organic or inorganic base, such as an amine or a metal hydroxide, such as potassium hydroxide, in the reaction mixture also benefits the conversion.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

REFERENCES

The following references to the extent that they provide exemplary procedural or other details supplementary to those set forth herein, are specifically incorporated herein by reference.

1. Lewis, N. S.; Nocera, D. G., Proc. Natl. Acad. Sci. U. S. A. 2006, 103, 15729-15735.
2. Whitesides, G. M.; Crabtree, G. W., Science 2007, 315, 796-798.
3. Moriarty, P.; Honnery, D., Int. J. Hydrogen Energy 2009, 34, 31-39.
4. Moriarty, P.; Honnery, D., Int. J. Hydrogen Energy 2010, 35, 12374-12380.
5. Turner, J. A., Science 2004, 305, 972-974.
6. Armaroli, N.; Balzani, V., ChemSusChem 2011, 4, 21-36.
7. Felderhoff, M.; Weidenthaler, C.; von Helmolt, R.; Eberle, U., Phys. Chem. Chem. Phys. 2007, 9, 2643-2653.
8. Sakintuna, B.; Lamari-Darkrim, F.; Hirscher, M., Int. J. Hydrogen Energy 2007, 32, 1121-1140.
9. Yueruem, Y.; Taralp, A.; Veziroglu, T. N., Int. J. Hydrogen Energy 2009, 34, 3784-3798.
10. Suh, M. P.; Park, H. J.; Prasad, T. K.; Lim, D.-W., Chem. Rev. 2012, 112, 782-835.
11. Peng, B.; Chen, J., Energy & Environmental Science 2008, 1, 479-483.
12. Demirci, U. B.; Miele, P., Energy & Environmental Science 2011, 4, 3334-3341.
13. Sanyal, U.; Demirci, U. B.; Jagirdar, B. R.; Miele, P., ChemSusChem 2011, 4, 1731-1739.
14. Enthaler, S., ChemSusChem 2008, 1, 801-804.
15. Joo, F., ChemSusChem 2008, 1, 805-808.
16. Grasemann, M.; Laurenczy, G., Energy & Environmental Science 2012, 5, 8171-8181.
17. Mura, M. G.; De Luca, L.; Giacomelli, G.; Porcheddu, A., Adv. Synth. Catal. 2012, 354, 3180-3186, S3180/1-S3180/64.
18. Fellay, C.; Dyson, P. J.; Laurenczy, G., Angew. Chem. Int. Ed. 2008, 47, 3966-3968.
19. Loges, B.; Boddien, A.; Junge, H.; Beller, M., Angew. Chem., Int. Ed. 2008, 47, 3962-3965.
20. Fukuzumi, S.; Kobayashi, T.; Suenobu, T., ChemSusChem 2008, 1, 827-834.
21. Zhou, X.; Huang, Y.; Xing, W.; Liu, C.; Liao, J.; Lu, T., Chem. Commun. 2008, 3540-3542.
22. Boddien, A.; Loges, B.; Junge, H.; Gaertner, F.; Noyes, J. R.; Beller, M., Adv. Synth. Catal. 2009, 351, 2517-2520.
23. Ojeda, M.; Iglesia, E., Angew. Chem. Int. Ed. 2009, 48, 4800-4803.
24. Ting, S.-W.; Cheng, S.; Tsang, K.-Y.; van der Laak, N.; Chan, K.-Y., Chem. Commun. 2009, 7333-7335.
25. Himeda, Y., Green Chem. 2009, 11, 2018-2022.
26. Boddien, A.; Loges, B.; Gaertner, F.; Torborg, C.; Fumino, K.; Junge, H.; Ludwig, R.; Beller, M., J. Am. Chem. Soc. 2010, 132, 8924-8934.
27. Bulushev, D. A.; Beloshapkin, S.; Ross, J. R. H., Catal. Today 2010, 154, 7-12.
28. Huang, Y.; Zhou, X.; Yin, M.; Liu, C.; Xing, W., Chem. Mater. 2010, 22, 5122-5128.
29. Scholten, J. D.; Prechtl, M. H. G.; Dupont, J., ChemCatChem 2010, 2, 1265-1270.
30. Majewski, A.; Morris, D. J.; Kendall, K.; Wills, M., ChemSusChem 2010, 3, 431-434.
31. Zhou, X.; Huang, Y.; Liu, C.; Liao, J.; Lu, T.; Xing, W., ChemSusChem 2010, 3, 1379-1382.
32. Boddien, A.; Mellmann, D.; Gaertner, F.; Jackstell, R.; Junge, H.; Dyson, P. J.; Laurenczy, G.; Ludwig, R.; Beller, M., Science 2011, 333, 1733-1736.
33. Solymosi, F.; Koos, A.; Liliom, N.; Ugrai, I., J. Catal. 2011, 279, 213-219.
34. Tanaka, R.; Yamashita, M.; Chung, L. W.; Morokuma, K.; Nozaki, K., Organometallics 2011, 30, 6742-6750.
35. Tedsree, K.; Li, T.; Jones, S.; Chan, C. W. A.; Yu, K. M. K.; Bagot, P. A. J.; Marquis, E. A.; Smith, G. D. W.; Tsang, S. C. E., Nat. Nanotechnol. 2011, 6, 302-307.
36. Luo, Q.; Feng, G.; Beller, M.; Jiao, H., J. Phys. Chem. C 2012, 116, 4149-4156.
37. Hull, J. F.; Himeda, Y.; Wang, W.-H.; Hashiguchi, B.; Periana, R.; Szalda, D. J.; Muckerman, J. T.; Fujita, E., Nat. Chem. 2012, 4, 383-388.
38. Mori, K.; Dojo, M.; Yamashita, H., ACS Catalysis 2013, 3, 1114-1119.
39. Gan, W.; Snelders, D. J. M.; Dyson, P. J.; Laurenczy, G., ChemCatChem 2013, 5, 1126-1132.

40. Wang, Z.-L.; Yan, J.-M.; Ping, Y.; Wang, H.-L.; Zheng, W.-T.; Jiang, Q., Angew. Chem. Int. Ed. 2013, 52, 4406-4409.
41. Wang, Z.-L.; Yan, J.-M.; Wang, H.-L.; Ping, Y.; Jiang, Q., J. Mater. Chem. A 2013, 1, 12721-12725.
42. Zell, T.; Butschke, B.; Ben-David, Y.; Milstein, D., Chemistry - A European Journal 2013, 19, 8068-8072.
43. Oldenhof, S.; de Bruin, B.; Lutz, M.; Siegler, M. A.; Patureau, F. W.; van der Vlugt, J. I.; Reek, J. N. H., Chem. Eur. J. 2013, 19, 11507-11511.

The invention claimed is:

1. A method to produce hydrogen from formic acid comprising the step of contacting formic acid with a complex comprising a ligand and a metal or metal ion, wherein the ligand is a compound according to formula (I), or a deprotonated version thereof, and the ligand is associated with the metal or metal ion, wherein formula (I) comprises:

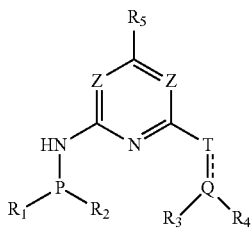

wherein $R_1$ and $R_2$, are each independently alkyl$_{(C \leq 12)}$, aryl$_{(C \leq 12)}$, aralkyl$_{(C \leq 12)}$, or a substituted version of any of these groups;
$R_3$, and $R_4$, if present, are each independently alkyl$_{(C \leq 12)}$, aryl$_{(C \leq 12)}$, aralkyl$_{(C \leq 12)}$, or a substituted version of any of these groups;
$R_5$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;
each Z, independently, is $CR_6$, N or P;
$R_6$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;
T is a N, $NR_7$, $CR_8$, or $CR_9R_{10}$;
$R_7$, $R_8$, $R_9$ and $R_{10}$ are each independently a hydrogen, alkyl$_{(C \leq 12)}$, aryl$_{(C \leq 12)}$, aralkyl$_{(C \leq 12)}$, or a substituted version of any of these groups;
Q is P or N;
optionally, wherein T and Q, together, form a 5 or 6 membered heterocyclic ring;
wherein the heterocyclic ring can optionally be substituted with one or more heteroatoms and or one or more sites of the heterocyclic ring are substituted with one or more alkyl$_{(C \leq 12)}$, aryl$_{(C \leq 12)}$, aralkyl$_{(C \leq 12)}$, or a substituted version of any of these groups, and optionally wherein the heterocyclic ring can have a fused ring attached thereto, provided when T and Q form a 5 or 6 membered heterocyclic ring, $R_3$ and $R_4$ are not present; and
- - - - - - designates a single bond or a double bond.

2. The method of claim 1, wherein T is NH and Q is P.
3. The method of claim 2, wherein $R_1$, $R_2$, $R_3$ and $R_4$ are each an alkyl$_{(C \leq 12)}$.
4. The method of claim 3, wherein $R_1$, $R_2$, $R_3$ and $R_4$ are each a t-butyl group.
5. The method of claim 1, wherein T is $CH_2$ and Q is N.
6. The method of claim 5, wherein $R_1$, $R_2$, $R_3$ and $R_4$ are each an alkyl$_{(C \leq 12)}$.

7. The method of claim 6, wherein $R_1$ and $R_2$ are t-butyl groups and $R_3$ and $R_4$ are ethyl groups.
8. The method of claim 1, wherein T is C, Q is N and T and Q form a 5 membered heterocyclic ring having the following formula:

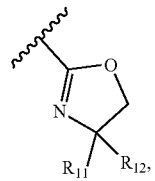

wherein $R_{11}$ and $R_{12}$, each independently, are a hydrogen atom or alkyl$_{(C \leq 12)}$, aryl$_{(C \leq 12)}$, aralkyl$_{(C \leq 12)}$, or a substituted version of any of these groups.
9. The method of claim 8, wherein $R_{11}$ and $R_{12}$ are both methyl groups.
10. The method of claim 1, wherein the complex further comprises a second ligand, wherein the second ligand is a halide or a hydrogen atom.
11. The method of claim 10, wherein the complex further comprises a third ligand, wherein the third ligand is carbon monoxide.
12. The method of claim 1, wherein substantially no carbon monoxide is produced.
13. The method of claim 12, wherein no carbon monoxide is produced.
14. The method of claim 1, wherein the metal or metal ion is a Group 8 metal or metal ion.
15. The method of claim 1, wherein the catalyst has a turnover number from about 500 to about 500,000.
16. A method to produce hydrogen from formic acid comprising the step of contacting formic acid with a compound of formula (II):

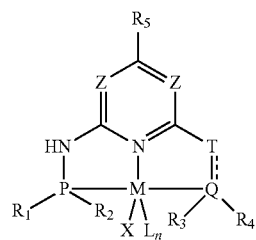

wherein $R_1$ and $R_2$, are each independently alkyl$_{(C \leq 12)}$, aryl$_{(C \leq 12)}$, aralkyl$_{(C \leq 12)}$, or a substituted version of any of these groups;
$R_3$, and $R_4$, if present, are each independently alkyl$_{(C \leq 12)}$, aryl$_{(C \leq 12)}$, aralkyl$_{(C \leq 12)}$, or a substituted version of any of these groups;
$R_5$ is a hydrogen atom or an alkyl$_{(C \leq 12)}$, aryl$_{(C \leq 12)}$, aralkyl$_{(C \leq 12)}$, or a substituted version of any of these groups;
each Z, independently, is $CR_6$, N or P;
$R_6$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;
M is a metal or metal ion that is a group 8 metal or metal ion;
L is a neutral or an anionic ligand;
n is 0, 1 or 2;

X is a halide or a hydrogen atom;

T is a N, $NR_7$, $CR_8$, or $CR_9R_{10}$;

$R_7$, $R_8$, $R_9$ and $R_{10}$ are each independently a hydrogen, alkyl$_{(C \leq 12)}$, aryl$_{(C \leq 12)}$, aralkyl$_{(C \leq 12)}$, or a substituted version of any of these groups;

Q is P or N;

optionally, wherein T and Q, together, from a 5 or 6 membered heterocyclic ring;

wherein the heterocyclic ring can optionally be substituted with one or more heteroatoms and or one or more sites of the heterocyclic ring are substituted with one alkyl$_{(C \leq 12)}$, aryl$_{(C \leq 12)}$, aralkyl$_{(C \leq 12)}$, or a substituted version of any of these groups, and optionally wherein the heterocyclic ring can have a fused ring attached thereto, provided when T and Q form a 5 or 6 membered heterocyclic ring, $R_3$ and $R_4$ are not present; and ------ designates a single bond or a double bond.

17. The method of claim 16, wherein T is NH and Q is P.

18. The method of claim 16, wherein T is $CH_2$ and Q is N.

19. A method to produce hydrogen from formic acid comprising the step of contacting formic acid with a compound of formula (III):

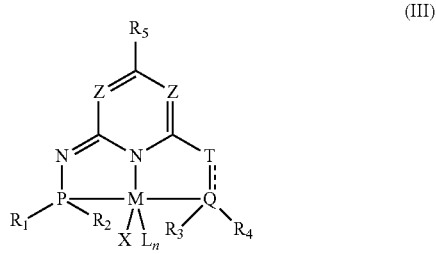

(III)

wherein $R_1$ and $R_2$, are each independently alkyl$_{(C \leq 12)}$, aryl$_{(C \leq 12)}$, aralkyl$_{(C \leq 12)}$, or a substituted version of any of these groups;

$R_3$, and $R_4$, if present, are each independently alkyl$_{(C \leq 12)}$, aryl$_{(C \leq 12)}$, aralkyl$_{(C \leq 12)}$, or a substituted version of any of these groups;

$R_5$ is a hydrogen atom or an alkyl$_{(C \leq 12)}$, aryl$_{(C \leq 12)}$, aralkyl$_{(C \leq 12)}$, or a substituted version of any of these groups;

each Z, independently, is $C_6$, N or P;

$R_6$ is a hydrogen atom or an alkyl$_{(C \leq 12)}$, aryl$_{(C \leq 12)}$, aralkyl$_{(C \leq 12)}$, amino, hydroxyl, alkoxyl or a substituted version of any of these groups;

T is a N, $NR_7$, $CR_8$, or $CR_9R_{10}$;

$R_7$, $R_8$, $R_9$ and $R_{10}$ are each independently a hydrogen, alkyl$_{(C \leq 12)}$, aryl$_{(C \leq 12)}$, aralkyl$_{(C \leq 12)}$, or a substituted version of any of these groups;

Q is P or N;

M is a metal or metal ion that is a group 8 metal or metal ion;

L is a neutral or an anionic ligand;

n is 0, 1 or 2;

X is a halide or a hydrogen atom; and optionally, wherein T and Q, together, form a 5 or 6 membered heterocyclic ring;

wherein the heterocyclic ring can optionally be substituted with one or more heteroatoms and or one or more sites of the heterocyclic ring are substituted with one alkyl$_{(C \leq 12)}$, aryl$_{(C \leq 12)}$, aralkyl$_{(C \leq 12)}$, or a substituted version of any of these groups, and optionally wherein the heterocyclic ring can have a fused ring attached thereto, provided when T and Q form a 5 or 6 membered heterocyclic ring, $R_3$ and $R_4$ are not present; and ------ designates a single bond or a double bond.

20. The method of claim 19, wherein T is NH and Q is P.

21. The method of claim 19, wherein T is $CH_2$ and Q is N.

* * * * *